United States Patent [19]

Schmidt et al.

[11] 3,967,928

[45] July 6, 1976

[54] METHOD FOR QUANTITATIVELY ANALYZING SUBSTANCES CONTAINING ELEMENTS OTHER THAN CARBON, HYDROGEN AND OXYGEN AND VOLATILE ORGANIC COMPOUNDS

[75] Inventors: Donald D. Schmidt; Gary L. Jewett; Richard G. Melcher; Ritchie A. Wessling, all of Midland, Mich.

[73] Assignee: The Dow Chemical Company, Midland, Mich.

[22] Filed: Mar. 22, 1974

[21] Appl. No.: 454,032

[52] U.S. Cl. .................................. 23/232 R; 73/23; 250/362
[51] Int. Cl.² ................. G01N 31/06; G01N 23/00
[58] Field of Search ................... 23/230 R, 232 R; 423/449; 252/421, 444; 73/23; 250/302, 362

[56] References Cited
UNITED STATES PATENTS

| | | | |
|---|---|---|---|
| 3,516,791 | 6/1970 | Evans et al. | 252/421 X |
| 3,711,251 | 1/1973 | Goodson et al. | 23/232 R |
| 3,832,306 | 8/1974 | Hackett et al. | 423/449 X |
| 3,840,649 | 10/1974 | Feay et al. | 423/449 X |

OTHER PUBLICATIONS

Barton et al., *J. Colloid & Interface Sci.*, vol. 44, pp. 50–56 (1973).
*Chem. Abstr.*, vol. 77:165678e (1972).
*Chem. Abstr.*, vol. 79:126863h (1973).

*Primary Examiner*—Morris O. Wolk
*Assistant Examiner*—Timothy W. Hagan
*Attorney, Agent, or Firm*—Ronald G. Brookens

[57] ABSTRACT

Method for quantitatively analyzing substances containing elements other than carbon, hydrogen and oxygen by (1) adsorbing such substances on a particulate, substantially dust and contaminant free carbonized product prepared by (A) first partially dehydrochlorinating a normally crystalline vinylidene chloride polymer at temperatures below the melting point of such polymer to an extent of at least about 5 percent of theoretical HCl loss, then (B) completing the dehydrochlorination of such material, in the substantial absence of oxygen, by heating the material to carbonizing temperatures of from about 600°C to about 1200°C; then (2) analyzing the substance adsorbed on such carbonized product.

10 Claims, No Drawings

METHOD FOR QUANTITATIVELY ANALYZING SUBSTANCES CONTAINING ELEMENTS OTHER THAN CARBON, HYDROGEN AND OXYGEN AND VOLATILE ORGANIC COMPOUNDS

BACKGROUND OF THE INVENTION

Carbon prepared by controlled pyrolysis of vinylidene chloride polymers (Saran carbon) has been described rather extensively in the literature, e.g., see the article by Ainscough, A. N., Dollimore, D., and Heal, G. R., "The Adsorption Characteristics of Polyvinylidene Chloride Carbon", Carbon 11, 189–197 (1973); and "Thermodynamics of Polyvinylidene Chloride in the Solid State" by Wessling, R. A. and Bohme, R. D. in Journal of Applied Polymer Science, Vol. 16, pp 1761–1778 (1972).

The kinetics of the dehydrochlorination reaction have also been discussed, e.g., by: Dacey, J. R., and Cadenhead, D. A. (The Royal Military College of Canada, Kingston, Ontario), "The Formation of Carbon from Polyvinylidene Chloride", Proceedings of the Fourth Conference on Carbon, Pergammon Press, N.Y. (1960), pp. 315–319; Everett, D. H., Redman, E., and (in part) Miles, A. J., and Davies, D. H. (The University, Bristol), "Saran Charcoals: Some Observations of Their Preparation and Adsorptive Properties", Fuel 42, 219–228 (1963); Fredler, A., and Fitzer, E. (Universitat Karlsruhe), "Kinetics for the Pyrolysis of Polyvinylidene Chloride", 3rd Conf. on Ind. Carbons and Graphite, 131–135 (1970) (London: Soc. of Chem. Ind.); and Burnett, G. M., Haldon, R. A. (The Univ. Aberdeen), and Hay, J. N. (The Univ., Birmingham), "Dehydrochlorination of Polymers - I. Polyvinylidene Chloride", Eur. Polymer J. 3, 449–457 (1967).

The morphology of carbon prepared from vinylidene chloride polymers has been discussed by: Bailey, A., and Everett, D. H. (U. of Bristol), "New Evidence for the Fine Structure of Porous Carbons", Nature 211, 1082–1083 (1966); Bailey, A., and Everett, D. H. (University of Bristol), "Morphology of Poly(vinylidene chloride) and of Carbons Resulting from its Pyrolysis", Journal of Polymer Science, A-2, 7, 87–104 (1969); Adams, L. B., Boucher, E. A., Cooper, R. N., and Everett, D. H. (U. of Bristol) "Preparation, Structure and Properties of Saran Carbon Fibres and Powders", 3rd Conf. on Ind. Carbons and Graphite, 478–482 (1970) (London: Soc. of Chem. Ind.); Boult, E. H., Campbell, H. G., and Marsh, H. (U. of Newcastle-upon-Tyne), "The Carbonization of Polyvinylidene Chloride — an Investigation using Scanning Electron Microscopy", Carbon 7, 700–701 (1969); and Franklin, Rosaline E., "Crystallite Growth in Graphitizing and Nongraphitizing Carbons", Royal Soc. London Proc. 209A, 196–218 (1951).

The molecular sieve properties of vinylidene chloride polymers, i.e., the ability of carbonized vinylidene chloride polymers to adsorb small molecules but not relatively large molecules, has also been discussed. The sizes of the micropores have been described to be from about 5 to 12 A in diameter, depending on polymer composition and heat treatment temperatures. Pertinent references include: Lamond T. G., Metcalf, J. E., III, and Walker, P. L., Jr. (Penn State), "6 A Molecular Sieve Properties of Saran-Type Carbons", Carbon 3, 59–63, (1965); Walker, P. L., Jr. (Penn State U., University Park, Pa.), "Molecular Sieves", Mineral Industries, Penn State Univ. 35 (4), 1–7 (1966); Dacey, J. R., and Thomas, D. G. (Royal Military College of Canada, Kingston, Ontario), "Adsorption on Saran Charcoal", Trans. Faraday Soc. 50, 740–748 (1954); and Barton, Stuart S., Boulton, Gordon L., Dacey, J. R., Evans, M. J. B., and Harrison, Brian H. (Royal Military College), "Heat of Immersion Studies on Carbon Formed from Polyvinylidene Chloride", J. Colloid Interface Sci. 44, 50–56 (1973).

Some workers have increased pore sizes of such carbons by post-activation of the carbon with carbon dioxide or water at elevated temperature, e.g., see the following articles: Walter, P. L., Jr., Lamond, T. G., and Metcalf, J. E., III (Penn State U.), "The Preparation of 4A and 5A Carbon Molecular Sieves", 2nd Conf. Ind. Carbon and Graphite, pp. 7–14, 1966 (London: Soc. Chem. Ind.); Culver, R. V., and Heath, N. S. (U. of Adelaide, South Australia), "Saran Charcoals. Part 1 - Activation and Adsorption Studies", Trans. Faraday Soc. 51, 1569–1575 (1955); Marsh, H., and Campbell, H. G., (U. of Newcastle upon Tyne), "The Characteristics of Microporous Carbons by Adsorption from Liquid and Vapor Phases", Carbon 9, 489–498 (1971); Lamond, T. G., and Marsh, H. (Newcastle upon Tyne), "The Surface Properties of Carbon. III — The Process of Activation of Carbons", Carbon 1, 293–307 (1964); and Siedlewski, Janusz, and Rychlicki, Gerald (Copernicus Univ. Forun, Poland), "Investigation of the carbon sorbents made from organic polymers. I. The porous structure and the adsorptive capacities of the Saran carbons activated by carbon dioxide and water vapor", Chemia Stosowana XV, 369–382 (1971).

Other literature describes dehydrochlorination of vinylidene chloride polymers with bases to produce carbon. Pertinent references are: Evans, Brian, and Flood, E. A. (National Research Council of Canada, Ottawa), "Low Temperature Carbonization of Polyvinylidene Chloride", Can. J. Chem. 45, 1713–1714 (1967); Evans, Brian, and Flood, Edward A. (assignors to Canadian Patents and Development Limited, Ottawa), "Microporous Carbon Preparation", U.S. Pat. No. 3,516,791, Patented June 23, 1970; and Barton, Stuart S., Boulton, Gordon, Harrison, B. H., and Kemp, William (Royal Military College of Canada), "Study of the Dehydrochlorination of Polyvinylidene Chloride by Alcholic Base, Using Ultra-Violet Adsorption Spectroscopy", Trans. Faraday Society 67, 3534–3539 (1971).

The following uses for carbonized vinylidene chloride polymers have also been disclosed: Badishe Arilin- & Soda Fabrik Aktiengesellschaft, "Chromatographic Separating Process and/or Analysis of Mixtures of Materials", Netherland Pat. No. 7,010,263, July 10, 1970; Kaiser, R. (Badishe Arilin- & Soda Fabrik AG), "Kohlenstoff-Molekularsieb", Chromatographia 3, 38–40 (1970); Zlatkis, A., Kaufman, H. R., and Durbin, D. E. (University of Houston), "Carbon Molecular Sieve Columns for Trace Analysis in Gas Chromatography", Journal of Chromotographic Science 8, 416–417 (1970); Lamond and Marsh, Carbon, Vol. 1, pp. 293–307 (1964), which article discloses adsorbing ethyl chloride on carbon to determine the surface area of such carbon; Rippberger, Willi, Oettinger, Willi, Kaiser, Rudolf, Pfitzner, Klaus, and Palm, Richard Adolf (BASF) "Manufacturing of Carbon by Cleavage of Hydrogen Halide from Polymeric Halogenated Hydrocarbons", German Pat. No. 2,104,657, Feb. 2, 1971; Reed, Madison W., Jr., and Schwemer, Warren C. (Advanced Technology Center, Inc., Arlington, Texas), "Method of Making a Porous Carbon Material", U.S. Pat. No. 3,647,551, Mar. 7, 1972; Reed, M. W., and Schwemer, W. C. (LTV Research Center, Dallas), "Porous Carbon Fuel Cell Electrodes from Polymer Precursors", *J. Electrochem. Soc.* 114, 582–585 (1967); and Mahajan, O. P., Walker, P. L., Jr. (Penn State), "Krypton Adsorption on Microporous Carbons and 5A Zeolite", *J. Coll. Interface Sci.* 29, 129–137 (1969).

Heretofore, however, it has been the practice in conducting quantitative analysis determinations, to adsorb the molecules to be analyzed on an activated carbon followed by desorption and analysis of the desorbed material. Exemplary of such prior knowledge is the disclosure in the article entitled "A Convenient Optimized Method for the Analysis of Selected Solvent Vapors in the Industrial Atmosphere" by White et al in *American Industrial Hygiene Association, J.* 31, 225–232 (1970). Conventionally used commercially available activated carbons, and particularly those derived from vegetable origins, e.g., coal and coconut shells, vary widely in composition. For example, the article entitled "Active Carbon" by Smisek and Cerny, Elsevier, New York, Page 62 (1970), discloses that an active carbon prepared from coconut shells contained 3.5 percent ash, including significant amounts, i.e., tenths of a percent, of potassium, aluminum, silicon, sodium and iron oxides and somewhat lesser amounts of magnesium, calcium, boron, copper, zinc and tin as well as trace amounts of lithium, rubidium, strontium and lead. The presence of these impurities prevents analytical determinations of substances while adsorbed on such carbons. Further, prior used active carbons are relatively soft resulting in carbon dusting and additional analytical uncertainty.

It is a primary object of the present invention to provide a means for quantitatively analyzing substances containing elements other than carbon, hydrogen and oxygen by adsorbing such substances on a carbonized material which is substantially dust and contaminant free and wherein such substances can be analyzed while still adsorbed on the carbon surface or, if desired, effectively desorbed for purposes of highly accurate analysis.

A further object is to provide an effective means for adsorbing relatively large amounts of highly volatile toxic vapors such as vinyl chloride or vinylidene chloride on a substantially dust and contaminant free carbon material, e.g., wherein such carbon is contained in an air-sampling tube as conventionally used to measure the concentrations of such materials in industrial locations.

SUMMARY OF THE INVENTION

The above and related objects are attained by utilization of a method comprising the sequential steps of (1) adsorbing the substances to be analyzed on a particulate, substantially dust and contaminant free carbonized product prepared by (A) first partially dehydrochlorinating a normally crystalline vinylidene chloride polymer, at a temperature below its melting point, to an extent of at least about 5 percent of theoretical HCl loss, then (B) completing the dehydrochlorination of such material, in the substantial absence of oxygen, by heating the material to carbonizing temperatures of from about 600°C to about 1200°C, then (2) analyzing the substance adsorbed on the carbonized product.

DESCRIPTION OF THE PREFERRED EMBODIMENTS

The normally crystalline vinylidene chloride polymers applicable for the purposes of the present invention include any such polymer capable of being present in a substantially dry, powdered form while having crystalline melting peaks of at least about 135°C, as determined by differential thermal analysis. Exemplary of an especially preferred material is the homopolymer of vinylidene chloride. Also useful, however, are those polymers containing at least about 70 weight percent of vinylidene chloride in the polymer molecule with the remainder of such molecule consisting of one or more ethylenically unsaturated comonomers. Exemplary of such comonomers are vinyl chloride, vinyl bromide, vinylidene bromide, vinyl acetate, vinyl propionate, acrylonitrile, acrylic acid, maleic acid, fumaric acid, itaconic acid, anhydrides of these acids, alkyl and aralkyl esters, having 8 or fewer atoms of carbon, of these acids, acrylamide, vinyl alkyl ethers, vinyl alkyl ketones, acrolein, allyl esters and ethers, butadiene, chloroprene, and 2,3-dichlorobutadiene.

The carbonized products utilized by the present invention are prepared by first dehydrochlorinating the normally crystalline vinylidene chloride polymer, with or without the presence of a base material and at a temperature below the melting point of the polymer, to an extent of at least about 5 percent of theoretical HCl loss. This partial dehydrochlorination provides sufficient crosslinking within the polymer molecule to convert the polymer from a plastic state to an infusible mass which can resist undesirable foaming of the polymer structure during subsequent dehydrochlorination and carbonization operations. The partially dehydrochlorinated polymer is then gradually heated, in the substantial absence of oxygen, to carbonizing temperatures within the range of from about 600°C to about 1200°C. A preferred method for preparing such carbonized products comprises an initial pyrolysis of from about 5 percent to about 60 percent of theoretical HCl loss by heating the polymer at temperatures between about 100°C and about 200°C over a period of several hours. Completion of dehydrochlorination and carbonization is then effected by raising the temperature slowly from about 200°C up to 600° C to 1200°C over an additional period of several hours. If the polymer is heated too fast, it melts and foams yielding an inferior carbon. If oxygen comes in contact with the polymer, at temperatures above about 400°C, the carbon is oxidized.

The carbon product used by the present invention is a hard, dust-free porous structure having a surface area of at least about 800 square meters per gram ($m^2/g$).

The materials capable of quantitative analysis by the method of the present invention include any material having a vapor pressure of at least 1 torr at room temperature.

Quantitative analysis techniques employed generally comprise (1) first analyzing the pure carbon for the elements of interest to determine a standard, (2) passing the compound, or mixture of compounds, containing the elements over the carbon, e.g., where such carbon is contained in a conventional air-sampling tube, and (3) then determining the amount of such elements adsorbed on the carbon by utilization of neutron activation or other conventional techniques. It is to be understood that the carbon having the elements adsorbed thereof, can be desorbed, if desired, e.g., by flushing the carbon with carbon disulfide and analyzing such solution.

The following examples illustrate the present invention.

EXAMPLE 1:

Preparation of Pure Carbon Beads (Saran Carbon) from a Normally Crystalline Vinylidene Chloride Polymer Substantially dry, particulate polyvinylidene chloride having crystalline melting peaks of greater than about 200°C was slowly heated in a closed vessel and under a nitrogen atmosphere from a temperature of about 100°C to about 200°C over a period greater than about 8 hours. This heat treatment resulted in the loss of about 50 percent of theoretical HCl and provided a hard, infusible particulate material. The product was then heated from a temperature of about 200°C, in the substantial absence of oxygen, to a temperature of about 1000°C over a period of about 24 hours. The resulting carbonized product was in the form of hard, substantially non-dusting uniform beads having a surface area of about 1100 m²/g and having a residual chlorine content of less than about .6% and a silicon content of less than 50 ppm.

EXAMPLE 2:

Collection and Determination of Hydrolytically Unstable Tetraethylorthosilicate and Zinc Oxide From Air Airborne concentrations of tetraethylorthosilicate and zinc oxide taken from the atmosphere were determined by pumping such concentrations through air sampling tubes containing a carbonized material as described in Example 1. The carbon was then analyzed for silicon (Si) and zinc (Zn) by activation analysis and the potential exposure to tetraethylorthosilicate and diethyl zinc (or zinc oxide), calculated.

An attempt was made to determine the collection efficiency of commercial activated charcoal for tetraethyl-O-silicate, but the activation data were inconclusive because of the high Si background of the charcoal (~12 mg. Si/gram charcoal). A carbon, made from Saran beads, as described in Example 1, was found to have low Si and Zn backgrounds. To determine the collection efficiency, a tube with divided sections was prepared. After starting the pump, 8 μl of tetraethyl-O-silicate was injected into the front cotton wad. Air was pulled through at the rate of one liter/min. for 30 min. This matches the approximate time and rate to be used in the actual sampling.

The two sections were analyzed separately by activation analysis and the results were compared to a standard prepared by placing the same amount of carbon in an activation sample vial and injecting 8 μl of tetraethyl-O-silicate. The front section showed 1200 μg Si, the back section <100 μg Si and the standard 1060 μg Si (theoretical 1080 μg Si). These data show good collection efficiency and accuracy for the procedure.

The analysis of silicon directly on the carbon was carried out using a Cockcraft Walton Neutron Generator. The nuclear reaction is $^{28}Si(n,p)Al^{28}$. The samples are irradiated for ten minutes and then counted for one minute in a gamma ray spectrometer. The $Al^{28}$ produced has a 2.3 minute half-life and an energy of 1.78 Mev. A standard Si solution was made from sodium silicate.

Zinc was determined by irradiating the samples for ten minutes in a neutron flux of 5 × 10-11 mv in a TRIGA reactor. The nuclear reaction is $^{68}Zn(n,\gamma)Zn^{69n}$. The 0.44 mev gamma energy was counted in a gamma spectrometer.

Calculations of the μg of Si and Zn were made based on standards and corrected for decay.

Each of ten individual samples taken indicated a total μg Si of less than 100 and a total μg Zn of less than 20. It is to be noted that 100 μg of Si is equivalent to 3 to 4 ppm tetraethylorthosilicate for a 20 to 30 liter air sample; and 20 μg of Zn is equivalent to 1 milligram per cubic meter (mg/m³) of zinc oxide and 1.5 to 1.7 mg/m³ diethyl zinc for a 20–30 liter air sample. The threshold limit value (TLV) for tetraethylorthosilicate is 20 ppm, and the TLV of zinc oxide is 5 mg/m³. Thus, the collection efficiency and detection sensitivities of the described carbon is well within required limits.

By way of comparison, substitution of the specified carbon produced from the normally crystalline vinylidene chloride polymer with a commercially available activated charcoal derived from coconut shells, provided inconclusive data due to the high impurity level of such activated charcoal, i.e., a silicon content of greater than about 12 mg of Si/gram of charcoal. Further, the silicon could not be effectively desorbed from such activated charcoal and subsequently analyzed, as the silicate hydrolyzed before desorption could be effected.

EXAMPLE 3:

Collection and Determination of Vinyl Chloride and Vinylidene Chloride Vapors from Air A. Breakthrough Studies A number of experiments were run to determine the optimum conditions for collecting vinyl chloride and vinylidene chloride from air both for long term sampling or personnel monitoring and for short term grab samples.

In an initial experiment three polyethylene tubes having an inside diameter of ¼ and a carbon bed 4 cm. in length containing Pittsburgh Activated Carbon having a surface area of about 1000 m²/g, were connected in series with glass tees. One arm of each tee was sealed with a septum so that air samples could be removed with a gas syringe for gas chromatographic (G.C.) analysis. A Saran bag containing 35.5 ppm vinylidene chloride and 50 ppm vinyl chloride in air was attached to the front end of the tubes and its contents pumped through at the rate of 0.5 and 0.2 liters/minute for thirty minutes. One ml air samples were taken and analyzed using a 12 ft × 1/8 in Carbowax 20M at 70°C, F.I.D. detector. Vinylidene chloride showed no breakthrough; however, vinyl chloride showed substantial breakthrough at both sampling rates as shown in Table I.

A similar experiment was performed using a polyethylene tube having an inside diameter of ¼ inch and a carbon bed 7 cm. in length and containing carbon beads as described in Example 1. After six hours, only 4% breakthrough of vinyl chloride was observed at 0.5 liter/minute and no breakthrough at the 0.2 liter/minute rate.

Smaller tubes for short term and grab samples were tested. Glass sampling tubes containing activated charcoal are commercially available for collecting volatile solvents in air. This type of tube was tested for collecting vinyl chloride and vinylidene chloride. Breakthrough was observed for vinyl chloride in 30 seconds and reached 100% breakthrough in less than 6 minutes. The commercial tube was repacked with an identical volume of the carbon beads as described in Example 1 and the experiment repeated. No breakthrough was observed after 7.5 minutes and 16% after 10 minutes. A slightly larger tube was prepared, and tested with 500 ppm vinyl chloride. This high concentration was pumped through at 0.8 liter/minute for 20.5 minutes before 1% breakthrough was observed.

The results of such testing is summarized in the following Table I.

vinyl chloride and vinylidene chloride collected is equivalent to the amount collected at 0.2 liter/minute, for eight hours at the 50 ppm and 25 ppm level respectively.

The carbon was unpacked from the tube, placed in a 10-ml serum bottle and sealed with a Fermpress metal collar. A hypodermic needle was inserted to vent the air while 5.0 ml of cold carbon disulfide was injected into the bottle. The hypodermic needle was removed immediately and the sample was allowed to set at room temperature, with occasional agitation, for 30 minutes. A standard was prepared by injecting 10 ml of cold carbon disulfide into an empty, sealed serum bottle, and injecting 4.8 ml of vinyl chloride gas and 7.6 $\mu$l of vinylidene chloride. The vent needle is not used when

TABLE I

Breakthrough of Vinyl Chloride Using Activated Carbon and Saran Carbon Beads

| Type of Tube | | Time | Rate (l/min) | Concentration Vinyl Chloride (ppm) | Vinylidene Chloride (ppm) | Breakthrough of Vinyl Chloride* |
|---|---|---|---|---|---|---|
| Pittsburgh Activated Carbon (polyethylene tube) - | Tube 1a | 30 min | 0.5 | 50 | 35.5 | 94% |
| | Tube 1b | 30 min | 0.5 | 50 | 35.5 | 56% |
| | Tube 1c | 30 min | 0.5 | 50 | 35.5 | 10% |
| | Tube 2a | 30 min | 0.2 | 50 | 35.5 | 38% |
| | Tube 2b | 30 min | 0.2 | 50 | 35.5 | 14% |
| | Tube 2c | 30 min | 0.2 | 50 | 35.5 | 7% |
| Saran Carbon Beads (polyethylene tube) | | 6 hr | 0.5 | 50 | 35.5 | 4% |
| | | 6 hr | 0.2 | 50 | 35.5 | none |
| Commercial Charcoal Glass Tube | | 30 sec | 1.0 | 500 | — | trace |
| | | 2.5 min | 1.0 | 500 | — | 31% |
| | | 6 min | 1.0 | 500 | — | 100% |
| Commercial Glass Tube Re-Packed with Saran Carbon Beads | | 7.5 min | 0.75 | 500 | — | none |
| | | 10.0 min | 0.75 | 500 | — | 16% |
| Saran Carbon Beads - Glass Tube | | 16 min | 0.8 | 500 | — | none |
| | | 20.5 min | 0.8 | 500 | — | 1% |
| | | 25 min | 0.8 | 500 | — | 20% |

*Vinylidene chloride showed no breakthrough under these sampling conditions.

B. Desorption-Recovery Studies

A sample tube packed with the carbon of the type as described in Example 1 was used to determine the desorption-recovery factor for vinyl chloride and vinylidene chloride. An inflated 10 liter Saran bag, into which 4.8 ml of vinyl chloride gas and 7.6 $\mu$l of vinylidene chloride had been injected, was attached to the sampling tube and pumped through at 0.5 liters/minute. The bag was reinflated and pumped through the tube to flush the bag of the compounds. The amount of preparing the standard since the vinyl chloride will dissolve in the carbon disulfide when it is injected slowly. Portions of the standard and the desorbed sample were analyzed by G.C. using a 6 ft × 1/8 in DC 200, 77°C F.I.D.

A recovery factor of 100% was determined for both vinyl chloride and vinylidene chloride.

The following Tables II and III illustrate the results of additional testing using various other volatile compounds.

TABLE II

Other Volatile Compounds Tested on Saran Carbon Beads

| Type of Tube | Compound Tested | Rate l/min | Time | Breakthrough | Recovery |
|---|---|---|---|---|---|
| Polyethylene Tube Injection on .7 gm | Methyl Chloride 100 ppm | 0.2 | 35 min | None | No Data |
| (a) Desorbed with CS$_2$ | Methacylonitrile | | | | 90% |
| (b) Desorbed with CS$_2$ + 20% Ether | Methacrylonitrile | | | | 99% |
| Steel Tube | Acrylonitrile | 0.5 | 10 min | None | 60% |

TABLE III

Desorption — Recovery of Mixed Solvents (% Recovery at 0.1 TLV level)

| | | Mixture A | | | | | Mixture B | |
|---|---|---|---|---|---|---|---|---|
| Type of Tube | Chlorothene | Methylene Chloride | Perchloroethylene | Toluene | Hexane | Acetone | MEK | Toluene |
| Commercial | | | | | | | | |

TABLE III-continued

| | Desorption — Recovery of Mixed Solvents (% Recovery at 0.1 TLV level) | | | | | | | |
|---|---|---|---|---|---|---|---|---|
| | Mixture A | | | | Mixture B | | | |
| Type of Tube | Chlorothene | Methylene Chloride | Perchloro-ethylene | Toluene | Hexane | Acetone | MEK | Toluene |
| Charcoal Tube | 92% | 91% | 96% | 100% | 100% | 84% | 90% | 100% |
| Saran Carbon Bead Tube | 99% | 94% | 95% | 100% | 107% | 92% | 100% | 100% |

The results may be over 100% because of the difficulty of injecting $\mu l$ amounts into an air-filled Saran bag.

The above data illustrate that the breakthrough time for vinyl chloride is unexpectedly about 12 times greater when using the herein prescribed Saran carbon as obtained when using conventionally employed activated charcoal having an equivalent surface area. The data also shows that the desorption-recovery of vinyl chloride and vinylidene chloride from such carbon, using carbon disulfide, is 100 percent. Such properties are extremely useful for effectively monitoring the presence of these toxic vapors.

EXAMPLE 4:

Collection and Determination of Bromochloromethane, Ethylene Dibromide and Bromoform in Air In a series of additional experiments of the nature as previously set forth in Examples 2 and 3 it was found that a wide range of halogenated hydrocarbons can be collected on either commercial activated charcoal tubes or Saran carbon tubes containing carbon of the type as described in Example 1. Activated charcoal tubes allow a sampling time of up to ½ hour at 1 liter/minute for most halogenated compounds without breakthrough of the tube. While these tubes are adequate for short term level monitoring in one location within a plan they lack the capacity of the similar sized Saran carbon tubes which is needed for determining time-weighted averages (TWA). A Saran carbon tube can be carried on a man while he performs various operations throughout a plant. The tube can then be analyzed and average exposure level calculated for each compound.

A. Collection Efficiency

Into a Saran bag containing 100 liters of dry filtered air was injected the following amounts of each compound to obtain the respective concentrations in ppm.

| Compound | Molecular Weight | TLV in ppm | $\mu l$s of Liquid 100 l Bag | Conc. (ppm, v/v) |
|---|---|---|---|---|
| Bromochloromethane | 129.29 | 200 | 50 | 193 |
| Ethylene dibromide | 187.88 | 20 | 10 | 28.3 |
| Bromoform | 252.77 | 0.5 | 2 | 5.8 |

Into the spout of the Saran bag was inserted the open end of a 0.5 mm I.D. glass disposable transfer pipette (Spectrum Cat. No. 269-183) containing 4 cm bed (0.7 gm) of carbon. The spout of the Saran bag and the glass pipette, from which the capillary tip had been removed, were held together with a link of rubber tubing. Short lengths of rubber tubing were also used to connect the pipette to an eight hour MSA pump (Model G) by way of a glass tee having one arm covered with a rubber septum.

The contents of the 100 liter bag was pumped through the Saran carbon bed at 0.2 liters/minute. The pump was checked every hour to insure a constant flow rate. Samples were taken at the tee at 15 minute intervals and analyzed by gas chromatography under the conditions below. After four hours, less than 0.5 ppm of each of the three compounds could be detected at the tee.

Chromatographic Conditions

Column — 20% DC-200 on 100/120 mesh Chromosorb W packed into 6 feet × ⅛ inch O.D. stainless steel tubing.
Column Temperature — 120°C.
Detector Temperature — 250°C.
Carrier Gas Flow ($N_2$) — 30 ml/min at 60 p.s.i.
Detector — flame ionization.
Instrument — Hewlett Packard 5700.
Sampling Loop Volume — 0.7 ml.

B. Recovery

At 0.2 l/minute a total of 48 liters of air would pass through the Saran carbon bed in four hours. The milligrams of a compound which would be collected in four hours if a compound were present at its respective TLV can be calculated from the following equation:

$$\text{Milligrams} = \frac{\text{ppm (vol/vol)} \times 48 \text{ liters} \times \text{molecular weight}}{24.5 \times 10^3 \text{ liters}}$$

These weights plus the density, the volume occupied by these weights and the volume and weight of each compound actually injected into 4 liters of air in a Saran bag appear below:

| Compound | Density | 20 4 | mg in 48 l at TLV | Volume in $\mu l$ | $\mu l$ in 4 l Air | mg |
|---|---|---|---|---|---|---|
| Bromochloromethane | 1.9344 | | 50.7 | 26.2 | 26 | 50 |
| Ethylene dibromide | 2.1701 | | 7.36 | 3.4 | 3.4 | 7.4 |
| Bromoform | 2.890 | | 0.25 | 0.0866 | 1.0 | 2.9 |

The recovery efficiencies were determined by adsorption of the contents of the 4 liter bags described above onto a bed of Saran carbon followed by desorption with carbon disulfide. After pumping the contents of each bag through a 4 cm bed of Saran carbon at 0.5 l/minute the bag was reinflated and the procedure repeated to ensure complete removal of the three compounds. The compounds were injected into the 4 liter bags after the spout of the bag was connected to the glass pipette containing the Saran carbon. This was done to eliminate loss of contents in handling the bag.

The beds of Saran carbon were desorbed with 5 mls of cold carbon disulfide for ½ hour with occasional shaking. A standard was prepared by injecting the same number of microliters of each compound into 5 mls of cold carbon disulfide as had been injected into the 4 liter bags. The recovery samples and standard were then compared under the following chromatographic conditions:

- Column — 10% DC-200 on 80/100 mesh Chromasorb P packed into 6 feet × 1/8 inch stainless steel tubing.
- Column, Injector and Detector Temperature — 100°C.
- Carrier Gas Flow ($N_2$) — 30 ml/minute.
- Detector — flame ionization.
- Injection size — 2 microliters.
- Instrument — Analytical Development Inc. Portable Gas Chromatograph Model 511.

Average peak heights were calculated for each peak from replicate injections of the standard and recovery samples. The following recovery factors were calculated from these peaks by dividing the average peak height of the standard into that of the sample for each compound. Duplicate recovery studies gave factors agreeing within 1%.

| | |
|---|---|
| Bromochloromethane | 96% |
| Ethylene dibromide | 89% |
| Bromoform | 100% |

As illustrated by the foregoing examples and disclosure, the present invention is particularly pertinent to recently increased interest in the ability to effectively monitor and control pollution, by providing the following significant advantages; (1) longer breakthrough times for highly volatile organic vapors such as vinyl chloride and vinylidene chloride which increases the sensitivity of the analysis technique and allows larger sampling volumes and prevents loss of the material being analyzed during sampling, (2) absence of dusting which increases the precision of analysis through greater ease in handling the carbon quantitatively and (3) enhanced desorption properties, e.g., when using carbon disulfide, which also allows greater precision in analytical determinations.

The method of the invention can be used for concentration and analysis of potential pollutants including organo-mercury compounds and thiophosphates and the like, which materials can be analyzed in the parts per billion range by passing waste streams through the pure carbon bed, followed by quantitative analysis while such materials remain adsorbed on such bed.

What is claimed is:

1. A method of quantitatively analyzing substances having a vapor pressure of at least 1 Torr at room temperature, said substances containing elements other than carbon, hydrogen and oxygen said method comprising the sequential steps of (1) adsorbing directly from the atmosphere and untreated sample of said substances on a particulate, substantially dust and contaminant free carbonized product prepared by (A) first partially dehydrochlorinating a normally crystalline vinylidene chloride polymer at temperatures less than the melting point of said polymer to an extent of at least about 5 percent of theoretical HCl loss, then (B) completing the dehydrochlorination of the partially dehydrochlorinated polymer, in the substantial absence of oxygen, by heating said polymer to carbonizing temperatures from about 600°C to about 1200°C, then (2) quantitatively analyzing for said substances while said substances remain adsorbed on said carbonized material.

2. The method of claim 1 wherein said particulate, substantially dust and contaminant free carbonized product has a surface area of at least about 800 $m^2/g$.

3. The method of claim 2 wherein said normally crystalline vinylidene chloride polymer is polyvinylidene chloride.

4. The method of claim 3 wherein the substance being analyzed is hydrolytically unstable tetraethylorthosilicate.

5. The method of claim 3 wherein the substance being analyzed is vinyl chloride monomer.

6. The method of claim 3 wherein the substance being analyzed is vinylidene chloride monomer.

7. The method of claim 3 wherein the substance being analyzed is a brominated organic compound.

8. The method of claim 7 wherein said brominated organic compound is selected from the group consisting of bromochloromethane, ethylene dibromide and bromoform.

9. The method of claim 3 wherein the substance being analyzed is a mixture of volatile solvents.

10. The method of claim 3 wherein said substances are quantitatively analyzed by subjecting said substance to a source of neutron activation.

* * * * *